US011808766B2

(12) United States Patent
Chen et al.

(10) Patent No.: US 11,808,766 B2
(45) Date of Patent: *Nov. 7, 2023

(54) METHOD FOR GENERATING HIGH AFFINITY ANTIBODIES

(71) Applicant: Regeneron Pharmaceuticals, Inc., Tarrytown, NY (US)

(72) Inventors: Gang Chen, Yorktown Heights, NY (US); Robert Babb, River Edge, NJ (US); James P. Fandl, LaGrangeville, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 603 days.

This patent is subject to a terminal disclaimer.

(21) Appl. No.: 16/987,639

(22) Filed: Aug. 7, 2020

(65) Prior Publication Data

US 2020/0369783 A1 Nov. 26, 2020

Related U.S. Application Data

(63) Continuation of application No. 15/526,522, filed as application No. PCT/US2015/060523 on Nov. 13, 2015, now Pat. No. 10,752,698.

(60) Provisional application No. 62/079,899, filed on Nov. 14, 2014.

(51) Int. Cl.
| | |
|---|---|
| *C07K 16/00* | (2006.01) |
| *G01N 33/569* | (2006.01) |
| *C07K 16/22* | (2006.01) |
| *C07K 16/32* | (2006.01) |
| *G01N 33/50* | (2006.01) |

(52) U.S. Cl.
CPC ....... *G01N 33/56972* (2013.01); *C07K 16/00* (2013.01); *C07K 16/22* (2013.01); *C07K 16/32* (2013.01); *G01N 33/50* (2013.01); *C07K 2317/10* (2013.01); *C07K 2317/92* (2013.01); *C12N 2510/02* (2013.01)

(58) Field of Classification Search
CPC ............. G01N 33/53; G01N 33/56966; G01N 33/4915; G01N 33/582; G01N 33/50; G01N 33/56972; C07K 16/00; C07K 16/22; C07K 16/32; C07K 2317/92; C07K 2510/02
See application file for complete search history.

(56) References Cited

U.S. PATENT DOCUMENTS

| | | | |
|---|---|---|---|
| 8,497,138 B2 | 7/2013 | Burke et al. | |
| 10,337,000 B2 | 7/2019 | Bradley et al. | |
| 10,752,698 B2* | 8/2020 | Chen | C07K 16/00 |
| 2005/0048578 A1* | 3/2005 | Zhang | C40B 40/02 |
| | | | 435/7.1 |
| 2017/0327593 A1 | 11/2017 | Chen et al. | |

FOREIGN PATENT DOCUMENTS

| | | |
|---|---|---|
| WO | 2012/072814 A1 | 6/2012 |
| WO | 2015/040401 A1 | 3/2015 |

OTHER PUBLICATIONS

Franz et al. Ex vivo characterization and isolation of memory B cells with antigen tetramers. Blood 118 (2): 348-357 (Jul. 14, 2011).*
Tickle et al. High-Throughput Screening for High Affinity Antibodies. JALA 303-307 (Oct. 2009).*
Franz B. et al., "Ex Vivo Characterization and Isolation of Rare Memory B Cells With Antigen Tetramers", Blood 118(2):348-357 (Jul. 14, 2011).
Hoven M.Y. et al., "Detection and Isolation of Antigen-Specific B Cells by the Fluorescence Activated Cell Sorter (FACS)", Journal of Immunological Methods 117:275-284 (1989).
McLean G.R. et al., "Recognition of Human Cytomegalovirus by Human Primary Immunoglobulins Identifies an Innate Foundation to an Adaptive Immune Response", The Journal of Immunology 174:4768-4778 (2005).
Olsen O.A., "The Selected Lymphocyte Antibody Method: A Novel Approach for the Generation and Genetic Analysis of Human Cytomegalovirus (HCMV) Neutralizing Monoclonal IgG antibodies", Jan. 1, 1999 (Jan. 1, 1999), Retrieved from the internet: URL:https://open.library.ubc.ca/clRcle/collections/ubctheses/831/items/1.0089962, retrieved on Jan. 13, 2016, pp. 27-29, chapters 2 and 3.
Rathanaswami P. et al., "Demonstration of an In Vivo Generated Sub-Picomolar Affinity Fully Human Monoclonal Antibody to Interleukin-8", Biochemical and Biophysical Research Communications 334:1004-1013 (2005).
Tickle S. et al., "High-Throughput Screening for High Affinity Antibodies", JALA 14(5):303-307 (Oct. 2009).
Wang X. et al., "Human Immunoglobulin Variable Region Gene Analysis by Single Cell RT-PCR", Journal of Immunological Methods 244:217-225 (2000).
Communication from the European Patent Office dated Aug. 9, 2019 received in European Patent Application No. 15802270.7, enclosing a Third Party Observation.

(Continued)

*Primary Examiner* — Gailene Gabel
(74) *Attorney, Agent, or Firm* — Scully, Scott, Murphy & Presser, P.C.; Todd R. Samelman

(57) ABSTRACT

The present disclosure relates to a method for identifying cells that express antigen-specific antibodies with a high binding affinity for a monomeric antigen. Using fluorescence activated cell sorting, cells expressing high affinity antigen-specific antibodies are selected from a population of immune cells isolated from a mammal that has been immunized with or otherwise exposed to the antigen. Nucleic acids encoding the high affinity antibodies can then be cloned into other lymphoid and non-lymphoid cells where the antibody can be expressed and from which the antibodies can be secreted.

47 Claims, 6 Drawing Sheets

(56) References Cited

OTHER PUBLICATIONS

Communication from the European Patent Office dated Aug. 9, 2018 received in European Patent Application No. 15802270.7, enclosing a Third Party Observation.
International Search Report and Written Opinion dated Jan. 29, 2016 received in International Application No. PCT/US2015/060523.

* cited by examiner

METHOD FOR GENERATING HIGH AFFINITY ANTIBODIES

CROSS REFERENCE TO RELATED APPLICATIONS

This application is a continuation of U.S. patent application Ser. No. 15/526,522, filed May 12, 2017, which is a National Stage of Entry of International Application No. PCT/US2015/060523, filed Nov. 13, 2015, which claims the benefit of priority from U.S. Provisional Application No. 62/079,899, filed Nov. 14, 2014, the entire contents of which are incorporated herein by reference.

TECHNICAL FIELD OF THE INVENTION

The present invention generally relates to high-affinity antibodies. More particularly, the present invention relates to a method for selecting high affinity antibodies.

BACKGROUND OF THE INVENTION

High affinity is a desirable attribute for many therapeutic antibodies. The availability of high affinity monoclonal antibodies is crucial to the development of targeted immunotherapies. In many immunized animals, however, very high affinity antibodies are rare and standard methods for generating antibodies are inefficient at isolating high affinity antibodies.

Typically, monoclonal antibodies are obtained from mouse hybridomas, which most often result from the fusion of B lymphocytes from immunized mice with murine myeloma cells. The isolation of rare high affinity antibodies by hybridoma technology, however, is not efficient because of throughput limitations on hybridoma culture.

Another approach to producing high affinity antibodies involves the use of display technology to produce a lead antibody candidate from a phage, yeast or mammalian library. Though direct DNA isolation from B cells expressing antibodies may be utilized, DNA libraries are expressed in cell expression systems, such as phage, yeast, or bacterial systems, then "panned" or titrated to select for the antibodies having high affinities. Display technologies can provide high-quality protein libraries, although they provide limited diversity. Consequently, in vitro mutagenesis-based affinity maturation is frequently a next step in generating high affinity antibodies derived from such libraries.

Thus, a need exists for an efficient method to obtain, in quantity, antibodies that have the requisite specificity and high binding affinity in an efficient manner, without the need for several rounds of screening (such as "panning") or site-directed mutagenesis.

SUMMARY OF THE INVENTION

The present invention is based on the observation that cells expressing antibody with high affinity for an antigen of interest can be selected and enriched directly from a population of antibody-producing cells of varying affinities. The antibodies are thus selected directly from primary antibody-producing cells, prior to a single-cell isolation and collection, such as using fluorescence activated cell sorting (FACS). This provides a simple method for the production of high affinity antibodies from a cellular pool of primary antibody-producing cells that express antibodies with different affinities. The method obviates the need for time-consuming affinity selection after antibodies are cloned and expressed in host cells. Thus screening/selection of antigen-specific antibodies followed by site-directed mutagenesis to achieve in vitro affinity maturation to enhance binding affinity is unnecessary.

In one aspect, therefore, the invention relates to a method in which primary antibody-producing cells expressing an antigen-specific antibody are efficiently selected based on their binding properties in situ, then isolated using techniques for single-cell isolation, such as using fluorescence activated cell sorting (FACS), a high throughput screening method that can sample hundreds of millions of cells in a cell population. The cells expressing desirable high affinity antibodies can be identified and isolated directly from all of the cells producing antibodies (rather than from screening antibody libraries following cloning steps). The antibodies produced by the selected cells can then be cloned and reproduced recombinantly in host cells for direct use, thereby diminishing the number of steps taken while ensuring a higher probability of desirable antibodies.

In one aspect, the present invention relates to a method for the selection of antibodies that specifically bind an antigen of interest with high affinity. In some embodiments, the method may be used for efficient isolation of antibodies to a monomeric antigen with affinities ranging from about 0.1 pM to about 10 nM.

In one aspect, the invention relates to a method for selecting cells that express antibody exhibiting high binding affinity for an antigen of interest from a population of cells that express antibodies of different binding affinity for the antigen; the method comprising: contacting a population of primary antibody-producing cells with specificity to an antigen of interest with a low concentration of labeled antigen for a time sufficient for the labeled antigen to bind to antibody on the surface of the cells; washing the labeled antigen-bound cells with an appropriate buffer for a period of time from about 15 minutes to about 60 minutes; then isolating the antigen-bound cells. The isolation step may further comprise identifying the antigen-bound cells with an antigen-binding protein comprising a label for identification. The method may even further comprise contacting the cells with an antigen-binding protein comprising a fluorescent label; and using fluorescence-activated cell sorting, thus identifying single cells that have bound antigen and express an antibody that specifically binds the antigen of interest with high affinity. In certain embodiments, the cell population is contacted with a low concentration of labeled antigen between about 1 nM and about 15 nM, in some embodiments between about 2 nM and about 10 nM; and in some embodiments, the concentration of biotinylated antigen is about 5 nM. In some embodiments, the cells to which labeled antigen has bound will exhibit high fluorescence intensity (FI). The method further relates to a method for separating high affinity antibodies from low affinity antibodies, such as isolating the antibodies having a $K_D$ less than about 25 nM, or less than about 20 nM, or less than about 15 nM, or less than about 10 nM.

In a related aspect, the invention relates to a cell selection method wherein antigen-specific cells are contacted with biotinylated antigen. In this embodiment, the method further comprises fluorescent y labeled streptavidin. The concentration of biotinylated antigen is between about 1 nM and about 15 nM, in some embodiments between about 2 nM and about 10 nM; in some embodiments, the concentration of biotinylated antigen is about 5 nM.

In a related aspect, the method further comprises collecting the cells that exhibit high fluorescent intensity to obtain cells that express antibodies of high affinity for the antigen of interest.

Host cells comprising a nucleic acid molecule encoding the antibody isolated using the methods of the invention are also contemplated.

In yet another related aspect, the method relates to a method for selecting high affinity antigen-specific antibody-producing cells from a population of cells selected from the group consisting of plasma cells, B cells, hybridomas and other recombinant cells, plasma cell myelomas, and tissue-derived cells such as spleen, lymph node, bone marrow or peripheral blood.

These, and other objects, features and advantages of this invention will become apparent from the following detailed description of the various aspects of the invention taken in conjunction with the accompanying drawings.

BRIEF DESCRIPTION OF THE DRAWINGS

FIG. 3, unshaded bar) and 20 were derived from B cells sorted with ExTek (monomer; FIG. 3, shaded bar). 22% and 0% of antibodies derived from B cells sorted with Tie2-hFc or ExTek, respectively, had dissociation t1/2 of less than 5 minutes (FIG. 3). 34% and 5% of antibodies derived from B cells sorted with Tie2-hFc or ExTek, respectively, had dissociation t1/2 of less than 10 minutes. 44% and 20% of antibodies derived from B cells sorted with Tie2-hFc or ExTek, respectively, had t1/2 had dissociation t1/2 of less than 20 minutes (FIG. 3). Thus selecting B cells with monomeric ExTek protein enriched for antibodies with longer t1/2 than selecting B cells with the dimeric Tie2-hFc protein.

DETAILED DESCRIPTION OF THE INVENTION

Figure 1:
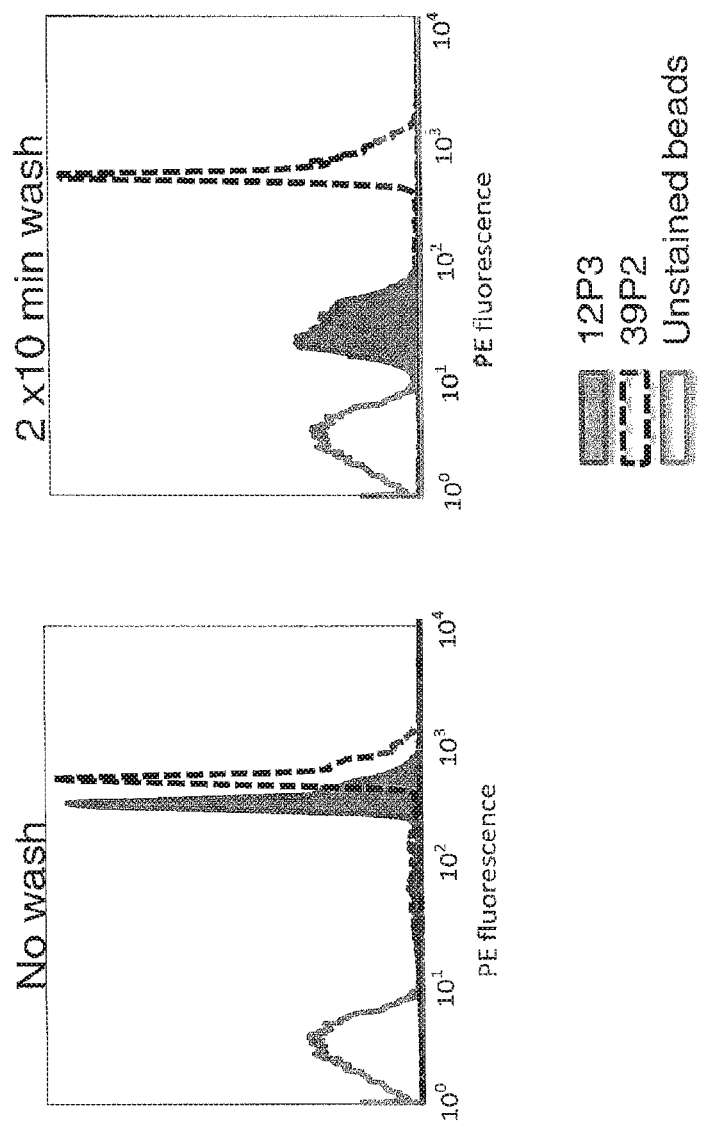
FIG. 1 shows an overlay of flow cytometry data for two Tie2 mAb-coated beads, either without wash or washed twice, before incubation with PE-streptavidin. Polystyrene microbeads were coated with monoclonal antibody 12P3 (shaded histogram) or 39P2 (dashed line histogram), two mouse monoclonal antibodies specific for human Tie2 protein, each having known binding dissociation ($t_{1/2}$) half-lives (1.46 min for 12P3 and 198.6 min for 39P2). Polystyrene microbeads conjugated with polyclonal anti-mFc capture antibodies were incubated with either 12P3 or 39P2 overnight. The next day, the beads were washed with PBS to remove unbound 12P3 and 39P2 antibodies and then incubated with 5 nM biotin-hExTek for one hour. Each sample was then divided into two aliquots. The beads in all samples were pelleted by centrifugation at 1,000 g for 4 minutes. Unbound biotin hExTek in the supernatants was removed. One aliquot for each Tie2 mAb was washed with PBS twice, 10 minutes duration each wash, then stained with PE-labeled streptavidin (right panel). The remaining aliquots were stained with PE-streptavidin without the wash step (left panel). After 45 minutes, the beads in all samples were pelleted by centrifugation, resuspended in PBS, and were analyzed by flow cytometry. A clear separation of high affinity antibodies and lower affinity antibodies can be seen in the histogram profiles when the samples were washed twice for 10 min/wash. The separation of the FACS profiles indicates that the high-affinity 39P2-coated beads can be isolated from a mixed beads population comprised of the 39P2 beads and 12P3 beads.

All publications, patents and other references cited herein are incorporated by reference in their entirety into the present disclosure.

In practicing the present invention, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

In the description that follows, certain conventions will be followed as regards the usage of terminology. Generally, terms used herein are intended to be interpreted consistently with the meaning of those terms as they are known to those of skill in the art.

The present invention may be used for efficient production of antibodies with affinities ranging from about 0.1 pM to about 25 nM, particularly having an $K_D$ less than 10 nM.

Antibody and antibodies as those terms are known in the art refer to antigen binding proteins of the immune system. The term antibody as referred to herein includes whole, full length antibodies having an antigen-binding region, and any fragment thereof in which the "antigen-binding portion" or "antigen-binding region" is retained; or single chains, for example, single chain variable fragment (scFv), thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant (CH) region. The heavy chain constant region is comprised of three domains, CH1, CH2 and CH3. Each light chain is comprised of a light chain variable region (abbreviated herein as VL) and a light chain constant CL region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with antigen.

The terms "antibody-producing cells" and "antibody-expressing cells" refer to cells that express antibody either naturally, i.e., as the result of B-cell activation or as the result of recombinant technology and genetic engineering. The term, therefore, encompasses lymphocytes of antigen-dependent B-cell lineage, including memory B-cells, plasmablasts and terminally differentiated plasma cells as well as recombinant cells such as hybridomas and non-lymphoid cells engineered to express antibodies. "Primary cells" refers to cells grown outside of their natural environment, such as tissue cells isolated from a mammal. In certain embodiments, primary antibody-producing cells are tissue-derived, such as from spleen, lymph node, bone marrow or peripheral blood. Furthermore, "antibody-producing cells" and "cells expressing antibodies" encompass cells in which the antibodies expressed are bound to or anchored in the cell membrane, i.e. cell surface antibodies, as well as cells that secrete antibody. Also, further antibody-producing cells may be derived from the starting primary antibody-producing cells or the primary antibody-producing cells selected by the methods of the invention. As such, cell lines, plasma cells, memory B-cells, hybridomas, plasma cell myelomas and recombinant antibody-expressing cells may be derived or isolated from primary antibody-producing cells prior to or following collection of antibody-producing cells expressing high-affinity antibodies. For example, primary antibody-producing cells may be fused to myeloma cells to make hybridomas, or otherwise immortalized, such as infected with a virus (e.g. EBV), or may be differentiated by cell sorting techniques based on protein markers expressed by particular B cell types. For example, selected antibody-producing cells expressing high-affinity antibodies may be sorted by FACS based on cell surface B cell markers.

"Binding affinity," as that term is known in the art, generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule for its binding partner can generally be represented by the dissociation equilibrium constant (KD or $K_D$). There is an inverse relationship between $K_D$ (molar) value and binding affinity, therefore the smaller the $K_D$ value (M), the higher the affinity. Thus "higher affinity" refers to antibodies that generally bind antigen stronger and/or faster and/or remain bound longer. Generally, a lower concentration (M) of antigen is needed to achieve the desired effect due to its stronger binding interaction.

The terms "low affinity" and "lower affinity" is a term used to reflect a weaker binding, such as a lower ability to form an interaction and therefore a larger $K_D$ value. Low-affinity antibodies generally bind antigen slowly and tend to dissociate readily.

The term "kd" (sec-1 or 1/s) refers to the dissociation rate constant of a particular antibody-antigen interaction, or the dissociation rate constant of an antibody, Ig, antibody-binding fragment, or molecular interaction. This value is also referred to as the koff value.

The term "ka" (M-1×sec-1 or 1/M) refers to the association rate constant of a particular antibody-antigen interaction, or the association rate constant of an antibody, Ig, antibody-binding fragment, or molecular interaction.

The term "KD" or "$K_D$" (M) refers to the equilibrium dissociation constant of a particular antibody-antigen interaction, or the equilibrium dissociation constant of an antibody, Ig, antibody-binding fragment, or molecular interaction. The equilibrium dissociation constant is obtained by dividing the ka with the kd.

A variety of methods of measuring binding affinity are known in the art, any of which can be used for purposes of the present invention. Binding affinities obtained using the method are in the range of about 0.1 pM to about 10 nM as determined by surface plasmon resonance.

The term "high affinity" antibody refers to those antibodies having a binding affinity, expressed as $K_D$, having a numerical value of about 0.1 pM to about 25 nM, or about 0.1 nM to about 10 nM. To this end, high affinity antibodies have a measured $K_D$ about $2.5 \times 10^{-9}$ M or less, about $1 \times 10^{-10}$ M or less, or about $0.5 \times 10^{-10}$ M or less, as measured by surface plasmon resonance, e.g., BIACORE™ or solution-affinity ELISA. Those of skill in the art will recognize that values for $K_D$ of antibodies may be represented numerically either as nE-z, or as $n \times 10^{-z}$, for example, 3.2E-12 is equivalent to $3.2 \times 10^{-12}$ and indicates a $K_D$ of 3.2 picomolar (pM).

The present invention provides a method to identify and isolate antigen-specific antibody-producing cells that express antibodies exhibiting a high binding affinity for an antigen of interest; the nucleic acids encoding these antibodies can then be cloned into host cells for mass production of the high affinity antibodies.

The present method avoids the use of mutation to enhance binding affinity. The method also obviates the need for panning of antibody libraries following expression of such antibodies in a host cell system.

Immunization and Collection of Primary Antibody-Producing Cells

Immunization of mammals can be done by any methods known in the art (see, for example, E. Harlow and D. Lane—Antibodies A Laboratory Manual, Cold Spring Harbor (1988); Malik and Lillehoj, Antibody techniques: Academic Press, 1994, CA). Antigen may be administered directly to a mammal, without adjuvant, or with adjuvant to aid in stimulation of the immune response. Adjuvants known in the art include, but are not limited to complete and incomplete Freund's adjuvant, MPL+TDM adjuvant system (Sigma), or RIBI (muramyl dipeptides) (see O'Hagan, Vaccine Adjuvant, by Human Press, 2000, NJ). Without relying on a particular theory, adjuvant can prevent rapid dispersal of polypeptide by sequestering the antigen in a local depot, and may contain factors that can stimulate host immune response.

The antigen of interest is administered as a protein, protein fragment, protein-fusion or DNA plasmid that contains the antigen gene of interest and expressing the antigen of interest using the host cellular expression machinery to express the antigen polypeptide in vivo, Various immunization techniques are known in the art. It is understood that the immunized mammal may be a human having been exposed to antigen and expressing humoral immunity for the antigen of interest.

In one embodiment, a non-human mammal is immunized with an antigen of interest and the animal's immune response to the antigen is monitored using an antigen-specific immunoassay. Once an appropriate immune response has been achieved, antibody-producing cells are collected from the immunized animal. Antibody-producing cells are collected from a number of sources, including but not limited to spleen, lymph node, bone marrow and peripheral blood.

For example, following immunization; splenocytes are harvested from an immunized animal, Following removal of red blood cells by lysis, IgG$^+$ antigen-positive B cells from the immunized animals are isolated from the cell population using the methods described herein.

In another embodiment, peripheral blood mononuclear cells (PBMCs) are harvested from a human or non-human mammal known to have humoral immunity to an antigen of interest, IgG$^+$, antigen-positive B cells having the highest affinities in the antibody-producing cell population can then be isolated for further processing in accordance with the methods of the invention.

Enrichment of a High-Affinity Population of Antibodies

To select for the cells that express antibodies exhibiting the highest binding affinity for the antigen of interest, the harvested cells are contacted with a low concentration, for example, from about 0.1 nM to about 25 nM, or from about 1 nM to about 20 nM or from about 2 nM to about 10 nM, of monomeric antigen that is labeled, for a time sufficient for the labeled antigen to bind to antibody on the surface of the immune cells; in some embodiments, exposure of the immune cells to labeled antigen for from about 5 to about 60 minutes is suitable. In some embodiments, the low concentration is less than about 10 nM. In other embodiments, the low concentration of antigen is about 9 nM, about 8 nM, about 7 nM, about 6 nM, about 5 nM, about 4 nM, about 3 nM, about 2 nM, about 1 nM. In still other embodiments, the antigen concentration is 5 nM. In some embodiments, the antigen concentration is less than about 1 nM. In another embodiment, the antigen concentration is 1 nM. In another embodiment, the antigen concentration is less than 1 nM. In other embodiments, the antigen is soluble.

In some embodiments, the label is biotin, e.g., the antigen is biotinylated. Antigen labels, otherwise called detection molecules, enable further detection of the antigen of interest bound to the antibody-producing cells. Detection may be made by immuno-staining with an antibody specific for the label or direct staining with a reagent that binds to the label. Numerous detection kits and techniques are well-known in the art.

Next; the cells are washed with buffer for a period of time from about 10 minutes to about 60 minutes to remove unbound antigen; multiple washes that total from 10 to 60 minutes may be used, e.g., 3 washes of 10 minutes or one 30-minute wash; 2-4 washes of 10-15 minutes each, etc. In one embodiment, washing the cells for a period of time comprising one (1) wash about 10 minutes, or about 15 minutes, or about 20 minutes, or about 25 minutes, or about 30 minutes, or about 35 minutes, or about 40 minutes, or about 45 minutes, or about 50 minutes, or about 55 minutes, or about 60 minutes total, may be used. In some embodiments; washing the cells for a period of time comprising two (2) washes each about 5 minutes, or about 10 minutes, or about 15 minutes or about 20 minutes, or about 25 minutes, or about 30 minutes per wash, may be used. Additional washing intervals are contemplated, essentially equivalent to those described herein.

Although in some circumstances the antigen of interest may be found in nature as a polymer, such as a dimer, the antigen may be engineered to a monomer for the purposes of the invention. For example, partial denaturation of polymers, protein engineering or protein fusion techniques may be employed by the skilled artisan. For example; the dimerization domain may be mutated or deleted to disallow dimerization.

The antigen of interest may be utilized as a dimer or other multimeric form (i.e. tetramer, heptamer, hexamer, etc.) for immunization purposes, however the same target epitopes of the antigen of interest are employed in a monomer for the purposes of enrichment of high-affinity antibodies.

Concurrently or successively, the cells may be detected as B cells, in particular IgG+IgM− cells (incubated with anti-B cell marker, anti-IgG or anti-Fc reagents, or the like) in the anticipation of next step single-cell isolation techniques. IgG or B cell detection reagents may be incubated with the cells prior to, during; or following the incubation with antigen of interest. B cell detection reagents are commercially available. (See also Huang, J. et al., 2013 *Nature Protocols,* 8(10): 1907-1915.)

Once unbound antigen has been removed, the selected cells are enriched for high-affinity antibodies. It has been unexpectedly found that by way of this invention a selected pool of cells expressing antibodies was enriched by achieving a high percentage of high-affinity antibodies isolated from the selected cells, such as greater than 50% 55%, 60%, 65%, 70%, 75%, 80%, or 85% isolated antibodies, or greater than 90%, 95%, 96%, 97% or 98% isolated antibodies are high-affinity antibodies.

Once unbound antigen has been removed, the cells are contacted with an antigen-binding protein comprising a detectable label, for example, a fluorescent label for the purposes of identifying the antigen-specific cells. In embodiments where the antigen has been biotinylated, a fluorescently labeled streptavidin is used for detection. In the instance where a detectable label is enzymatically activated, the cells are contacted with the appropriate enzyme to detect cells bearing bound antigen.

Single-Cell Sorting of Antibody-Producing Cells

Using fluorescence-activated cell sorting (FACS) to detect and isolate the enriched high-affinity antibody expressing cells is a highly efficient and sensitive tool for single-cell sorting. Protocols for single cell isolation by flow cytometry are well-known (Huang, J. et al, 2013, supra). To that end, cells that bind fluorescent antigen (or fluorescently-labeled streptavidin/biotinylated antigen) are detected and identified as cells that express antibodies that specifically bind the antigen of interest with high affinity, and are isolated to individual wells on 96-well, or 384-well plates. Once sorted, single cells may be propagated by common cell culture techniques for subsequent DNA preparation. Alternatively, antibody genes may be amplified from single B cells directly and subsequently cloned into DNA vectors.

Cells may be sorted and collected by alternative methods known in the art, including but not limited to manual single cell picking, limited dilution and B cell panning of adsorbed antigen, which are all well-known in the art (Rolink, et al., 1996 *J Exp Med* 183:187-194; Lightwood, D. et al, 2006 *J. Immunol. Methods* 316(1-2):133-43. Epub 2006 Sep. 18).

Isolated B cells may be fused with an immortal cell, such as a myeloma cell line, in order to create a hybridoma. Hybridoma techniques are well within the skill of the artisan (Harlow and Lane, 1988, supra). Isolated B cells may be further differentiated or sorted to identify specific B cell types, such as determination by cell surface or gene expression markers.

Recombinant Production of Antibodies

Once cells are collected, the DNA is prepared from the cells in order to recombinantly produce the antibodies. As mentioned above, B cells may be cultured, fused to myeloma cells or otherwise immortalized, such as infected with a virus (e.g. EBV), in order to make the DNA more abundant, as necessary, prior extracting DNA and cloning antibody genes directly from each sorted B cell. Briefly, genes encoding immunoglobulin variable heavy and light chains (i.e. VH, Ig Vκ and Vλ) are recovered using RT-PCR of mRNA isolated from the selected antibody-producing cells, as performed using conventional techniques, for example, as described by Wang et al. (*J. Immunol. Methods* 244:217-225) and described herein. Antibody genes are cloned into IgG heavy- and light-chain expression vectors and expressed via transfection of host cells.

For recombinant production of an antibody of the invention in a suitable host cell, the nucleic acid encoding the antibody genes are inserted into a replicable vector for further cloning (amplification of the DNA) or for expression (stably or transiently). Many vectors, particularly expression vectors, are available or may be engineered to comprise appropriate regulatory elements. An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an antibody-encoding nucleic acid molecule is comprised in a naked DNA or RNA vector, including, for example, a linear expression element (as described in, for instance, Sykes and Johnston, Nat Biotech 12:355-59 (1997)), a compacted nucleic acid vector (as described in for instance U.S. Pat. No. 6,077,835 and/or WO00/70087), or a plasmid vector such as pBR322, pUC 19/18, or pUC 118/

119. Such nucleic acid vectors and the usage thereof are well known in the art (see, for instance, U.S. Pat. Nos. 5,589,466 and 5,973,972).

An expression vector may alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

In certain embodiments, the vector comprises a nucleic acid molecule (or gene) encoding a heavy chain of the antibody and a nucleic acid molecule encoding a light chain of the antibody, wherein the antibody is produced by the B cell selected by a method of the invention. The vector utilized includes an expression vector comprising the nucleic acid molecules (genes) described wherein the nucleic acid molecule (gene) is operably linked to an expression control sequence suitable for expression in the host cell.

The choice of vector depends in part on the host cell to be used. Host cells include, but are not limited to, cells of either prokaryotic or eukaryotic (generally mammalian) origin.

In some embodiments, the host cell is a bacterial or yeast cell. In some embodiments, the host cell is a mammalian cell. In other embodiments, the host cell is selected from the group consisting of CHO (e.g. CHO K1, DXB-11 CHO, Veggie-CHO), COS (e.g. COS-7), stem cell, retinal cells, Vero, CV1, kidney (e.g. HEK293, 293 EBNA, MSR 293, MACK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell.

It will be appreciated that the full-length antibody (heavy chain and light chain comprising variable and constant regions) may be subsequently cloned into an appropriate vector or vectors. Alternatively, the Fab region of an isolated antibody may be cloned into a vector or vectors in line with constant regions of any isotype for the intended purpose. Therefore, any constant region may be utilized in the construction of isolated antibodies, including IgG1, IgG2, IgG3, IgG4, IgM, IgA, IgD, and IgE heavy chain constant regions, or chimeric heavy chain constant regions. Such constant regions can be obtained from any human or animal species depending on the intended use of the antibodies. Also, antibody variable regions or Fab region may be cloned in an appropriate vector(s) for the expression of the protein in other formats, such as ScFv, diabody, etc.

The invention provides a mammalian host cell encoding a nucleic acid molecule comprising a high affinity antibody specific for an antigen of interest, wherein a heavy chain variable region and a light chain variable region of the antibody were isolated from a B cell expressing the antibody, and wherein the B cell was selected from a population of cells from an immunized mammal with a low concentration of the antigen in monomeric form.

Determination of Antigen Binding Affinity

Binding affinities and kinetic constants of the antibodies derived from cells isolated using the method of the invention are determined in accordance with methods known in the art, for example, by surface plasmon resonance. In one embodiment, measurements are conducted at 25° C. on, for example, a Biacore 2000 or similar instrument. Antibodies are captured on an anti-human Fc sensor surface, and soluble monomeric protein is injected over the surface. Kinetic association ($k_a$) and dissociation ($k_d$) rate constants are determined by processing and fitting the data to a 1:1 binding model using curve fitting software. Binding dissociation equilibrium constants ($K_D$) and dissociative half-lives ($t_{1/2}$) are calculated from the kinetic rate constants as: $K_D(M)=k_a k_d$; and $t_{1/2}$ (min)=(ln2/(60·1$c_d$)).

EXAMPLES

Example 1. Separation of Micro Beads Coated with a Fast Dissociation Antibody from Micro Beads Coated with a Slow Dissociation Antibody by Flow Cytometry B cells from immunized mice express BCRs of varying affinity against an immunogen. In an experiment to demonstrate the feasibility of separating B cells by fluorescence-activated cell sorting based on antigen binding dissociation rates using labeled antigen (human ExTek.6His; see Lin, P. et al. *PNAS USA*, 1998 Jul. 21; 95(15); 8829-8834), polystyrene micro beads (cat. number MPFc-60-5, Spherotech, Lake Forest, Ill.) were coated with mAb 12P3 or 39P2, two mouse monoclonal antibodies against human Tie2 protein. The dissociation $t_{1/2}$ of the binding between these two antibodies and hExTek, a purified protein comprised of human Tie2 extracellular domain and a 6-His tag, is 1.46 min for 12P3 and 198.6 min for 39P2. Polystyrene beads conjugated with polyclonal anti-mFc capture antibodies were incubated with either 12P3 or 39P2 overnight. The next day, the beads were washed with PBS to remove unbound 12P3 and 39P2 antibodies and then incubated with 5 nM biotin-hExTek for one hour. Each sample was then divided into two aliquots. The beads in all samples were pelleted by centrifugation at 1,000 g for 4 minutes. Unbound biotin hExTek in the supernatants was removed. One aliquot of beads for each Tie2 mAb was washed with PBS twice, 10 minutes duration each wash, then stained with Phycoerythrin (PE)-labeled streptavidin. The remaining two aliquots were stained with PE-streptavidin without the wash step. 45 min later, the beads in all samples were pelleted by centrifugation, resuspended in PBS, and were analyzed by flow cytometry.

The results are shown in FIG. 1.

FIG. 1 shows an overlay of flow cytometry data for the two Tie2 mAb-coated beads, either without a wash step or washed twice, before incubation with PE-streptavidin. There was a clear separation in their profiles, when washed twice for 10 min each. The clear separation of the FAGS profiles indicates that the 39P2-coated beads could be isolated from a mixed beads population comprised of the 39P2 beads and 12P3 beads. Thus, it is likely that B cells expressing surface-anchored antibodies with fast or slow dissociation constants can be separated by using 5 nM of labeled antigen to label the B cells and incorporating a subsequent wash step before the addition of a secondary detection reagent such as phycoerythrin (PE)-streptavidin.

Figure 2:
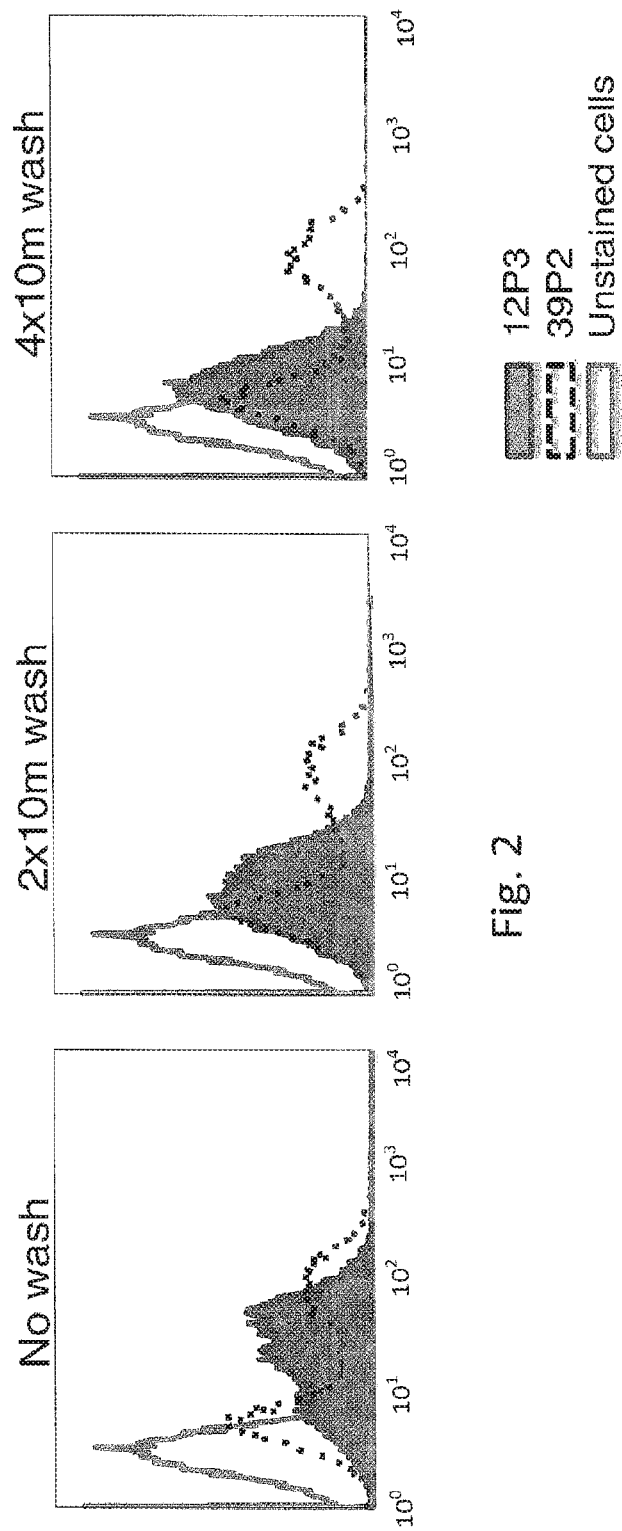
FIG. 2 demonstrates separation of hybridoma cells expressing a low affinity antibody from hybridoma cells expressing a high affinity antibody by flow cytometry. The hybridoma cell lines producing the 12P3 and 39P2 antibodies express membrane-anchored IgG as well as soluble IgG lacking transmembrane domain. The two hybridoma cell lines were incubated with 5 nM biotin-hExTek for one hour. The two antigen-bound cell populations were each divided into three aliquots. One aliquot for each cell line sample was given excess PE-streptavidin without the removal of biotin-hExTek and incubated for 30 minutes. In parallel, the other aliquots for each cell line sample were washed with excess PBS for either 20 minutes or 40 minutes, then stained with PE-streptavidin for 30 minutes. PE fluorescence of all cell samples was analyzed by FACS. The 39P2 cell line was comprised of two populations of cells as evidenced by two peaks (dashed line) with different levels of PE fluorescence on FACS: $PE^{high}$ and $PE^{low}$, due to differing levels of surface IgG expression. The mean fluorescence intensity of the $PE^{high}$ 39P2 cells (dashed line) did not change significantly when the cells were washed for either 20 min. or 40 min. prior to staining with PE-streptavidin. The PE fluorescence of the stained 12P3 cells mostly overlaps with the PE fluorescence of the $PE^{high}$ 39P2 cells. However, PE fluorescence of the 12P3 cells (shaded histogram) that were washed for either 20 min. or 40 min. following incubation with biotin-hExTek but prior to staining with PE-streptavidin was significantly less than the PE fluorescence of the $PE^{high}$ 39P2 cells, such that these two cell populations were well separated on FACS. The separation of the FACS histograms of the cell populations enables isolation of the $PE^{high}$ 39P2 cells from a mixture of $PE^{high}$ 39P2 and 12P3 cells by sorting for high PE cells on a flow cytometer.

Example 2. Separation of Hybridoma Cells Expressing a Low Affinity Antibody from Hybridoma Cells Expressing a High Affinity Antibody by Flow Cytometry The hybridoma cell lines producing the 12P3 and 39P2 antibodies expressed membrane-anchored IgG as well as soluble IgG lacking transmembrane domain. The 39P2 cell line contained two populations of cells with different levels of surface IgG expression. These two hybridoma cell lines were stained with 5 nM biotin-hExTek for one hour. The two stained cell populations were each divided into three aliquots. One aliquot for each cell line sample was given excess PE-streptavidin without the removal of biotin-hExTek and incubated for 30 minutes. In parallel, the other aliquots for each cell line sample were washed with excess PBS for either 20 minutes or 40 minutes, then stained with PE-streptavidin for 30 minutes. PE fluorescence of all cell samples was analyzed by FACS (FIG. 2). The 39P2 cell line was comprised of two populations of cells with different levels of PE fluorescence on FACS: $PE^{high}$ and $PE^{low}$, due to differing levels of surface IgG expression. The mean fluorescence intensity of the $PE^{high}$ 39P2 cells did not change significantly when the cells were washed for either 20 min or 40 min prior to staining with PE-streptavidin. The PE fluorescence of the stained 12P3 cells mostly overlaps with the PE fluorescence of the $PE^{high}$ 39P2 cells. However, PE fluorescence of the 12P3 cells that were washed for either 20 min or 40 min following incubation with biotin-hExTek but prior to staining with PE-streptavidin was significantly less than the PE fluorescence of the $PE^{high}$ 39P2 cells, such that these two cell populations were well separated on FACS. The separation of the FACS histograms of the cell populations enables isolation of the $PE^{high}$ 39P2 cells from a mixture of $PE^{high}$ 39P2 and 12P3 cells by sorting for high PE cells on a flow cytometer.

The results are shown in FIG. 2.

Example 3. Staining and Sorting Immunized B Cells with Monomeric Antigen Yielded More Antibodies with Slower Dissociate Rate than Staining and Sorting B Cells with Dimer Antigen VELOCIMMUNE® mice were immunized with a purified protein comprised of Tie2 extracellular domain and human Fc domain (Tie2-hFc). This protein is a dimer due to Fc:Fc association. After three injections of Tie2-hFc to boost immune response, mice were sacrificed and splenocytes were harvested. The splenocytes were pooled and divided into two aliquots. Cells in one aliquot were stained with 5 nM biotinylated Tie2-hFc protein and FITC-anti-mFc for 1 hour. In the meantime, the other half of the splenocyte pool was stained with 5 nM biotinylated ExTek and FITC-anti-mFc for 1 hour. The stained cells were washed for 10 minutes with PBS, then stained with SA-PE for one hour. The stained cells were washed once with PBS and were analyzed by flow cytometry on a MoFlo (Cytomation).

Single IgG positive and antigen positive B cells were sorted into separate wells on a 96-well plate. RT-PCR of antibody genes from these B cells was performed according to a method described by Wang and Stollar (Journal of Immunological Methods 2000; 244: 217-225). Briefly, cDNAs for each single B cell were synthesized via reverse transcriptase (RT) reaction (Superscript™ III, Invitrogen). Each resulting RT product was then split and transferred into two corresponding wells on two 96-well plates. One set of the resulting RT products was first amplified by PCR using a 5' degenerate primer specific for human IgG heavy chain variable region leader sequence and a 3' primer specific for mouse heavy chain constant region, to form an amplicon. The amplicon was then amplified again by PCR using a 5' degenerate primer set specific for framework 1 of human IgG heavy chain variable region sequence and a 3' degenerate primer set specific for framework 4 of human IgG heavy chain variable region sequence. The other set of the resulting RT products was first amplified by PCR using a 5' degenerate primer specific for human kappa light chain variable region leader sequence and a 3' primer specific for mouse kappa light chain constant region to form an amplicon. The amplicon was then amplified again by PCR using a 5' degenerate primer set specific for framework 1 of human kappa light chain variable region sequence and a 3' degenerate primer set specific for framework 4 of human kappa light chain variable region sequence. The heavy chain and light chain FOR products were cloned into antibody vectors containing human IgG1 heavy chain constant region and kappa light chain constant region, respectively. Recombinant hIgG1 antibodies were produced by transient transfection of CHO K1 cells. Dissociation constants of the binding between ExTek protein and 61 Tie2-specific antibodies present in these culture supernatants were determined on Biacore.

Figure 3:
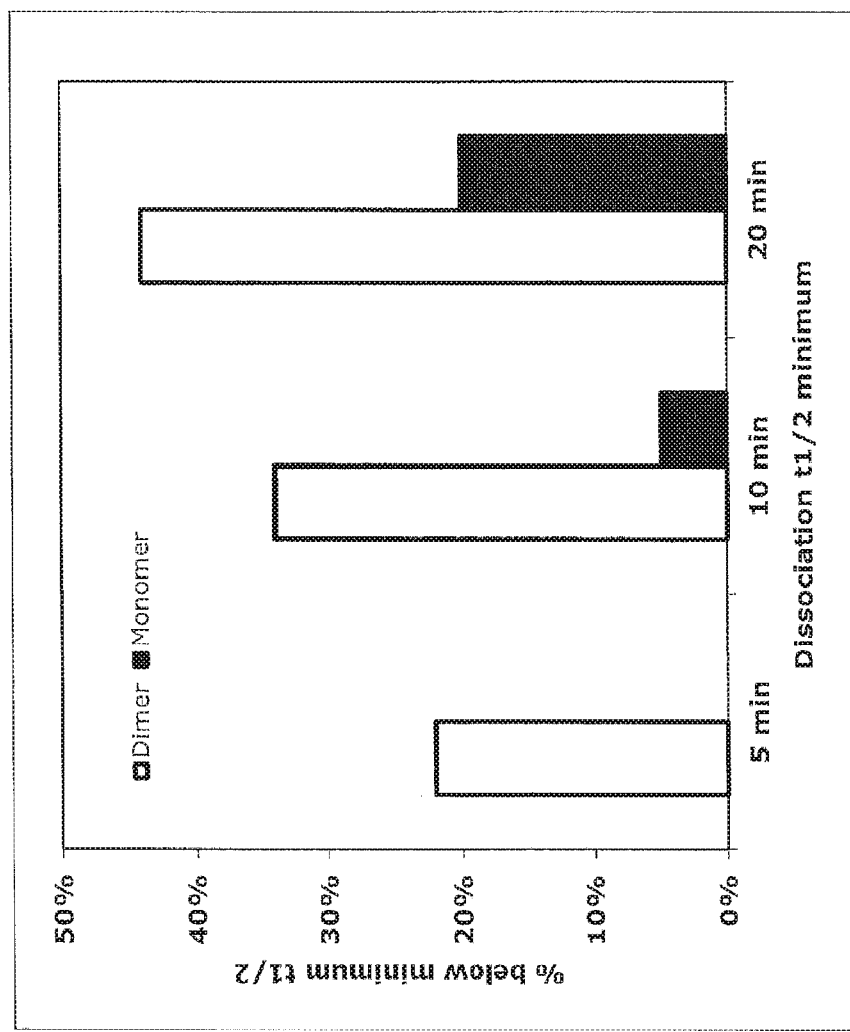
FIG. 3 shows that selecting immunized B cells with monomeric antigen yielded more antibodies with slower dissociate rate than staining sorting B cells with dimeric antigen. VELOCIMMUNE® mice were immunized with a purified protein comprised of Tie2 extracellular domain and human Fc domain (Tie2-hFc), Splenocytes from the immunized animals were harvested, pooled and divided into two aliquots. Cells in one aliquot were incubated with 5 nM biotinylated Tie2-hFc protein and FITC-anti-mFc for 1 hour. In the mean time, the other half of the splenocytes pool was incubated with 5 nM biotinylated ExTek and FITC-anti-mFc for 1 hour. The antigen-bound cells were washed twice with PBS, then stained with streptavidin (SA)-PE for one hour. The stained cells were washed once with PBS and were analyzed by flow cytometry on a MoFlo (Cytomation). Single IgG positive and antigen positive B cells were sorted into separate wells on a 96-well plate. RT-FOR of antibody genes from these B cells was performed according to a method described by Wang and Stollar (Journal of Immunological Methods 2000; 244: 217-225). Briefly, cDNAs for each single B cell were synthesized via reverse transcriptase (RT) reaction (Superscript™ III, Invitrogen). Each resulting RT product was then split and transferred into two corresponding wells on two 96-well plates. One set of the resulting RT products was first amplified by FOR using a 5' degenerate primer specific for human IgG heavy chain variable region leader sequence and a 3' primer specific for mouse heavy chain constant region, to form an amplicon. The amplicon was then amplified again by FOR using a 5' degenerate primer set specific for framework 1 of human IgG heavy chain variable region sequence and a 3' degenerate primer set specific for framework 4 of human IgG heavy chain variable region sequence. The other set of the resulting RT products was first amplified by PCR using a 5' degenerate primer specific for human kappa light chain variable region leader sequence and a 3' primer specific for mouse kappa light chain constant region to form an amplicon. The amplicon was then amplified again by PCR using a 5' degenerate primer set specific for framework 1 of human kappa light chain variable region sequence and a 3' degenerate primer set specific for framework 4 of human kappa light chain variable region sequence. The heavy chain and light chain FOR products were cloned into antibody vectors containing human IgG1 heavy chain constant region and kappa light chain constant region, respectively. Recombinant hIgG1 antibodies were produced by transient transfection of CHO K1 cells. Dissociation constants of the binding between ExTek protein and 61 Tie2-specific antibodies present in these culture supernatants were determined on Biacore. Among the 61 Tie2-specific antibodies, 41 were derived from B cells sorted with Tie2-hFc (dimer.

Among the 61 Tie2-specific antibodies, 41 were derived from B cells sorted with Tie2-hFc and 20 were derived from B cells sorted with ExTek. 22% and 0% of antibodies derived from B cells sorted with Tie2-hFc or ExTek, respectively, had dissociation $t_{1/2}$ of less than 5 minutes (shown in FIG. 3). 34% and 5% of antibodies derived from B cells sorted with Tie2-hFc or ExTek, respectively, had dissociation $t_{1/2}$ of less than 10 minutes. 44% and 20% of antibodies derived from B cells sorted with Tie2-hFc or ExTek, respectively, had dissociation $t_{1/2}$ of less than 20 minutes (FIG. 3). Thus, staining and sorting B cells with the monomeric ExTek protein enriched for antibodies with longer $t_{1/2}$ than staining and sorting B cells with the dimeric Tie2-hFc protein.

Example 4. Isolation and Production of High Affinity Erb3 Antibodies Generated Via Direct Isolation of Splenocytes A protein immunogen comprising the human Erb3 extracellular domain fused to mouse Fc (Erb3.mFc) was produced in CHO cells and purified. The Erb3.mFc protein was administered directly to VELOCIMMUNE® mice comprising DNA encoding human Immunoglobulin heavy and kappa light chain variable regions (Regeneron Pharmaceuticals, Inc., U.S. Pat. No. 6,596,541). The antibody immune response was monitored by an Erb3-specific immunoassay. When a desired immune response was achieved splenocytes were harvested. Red blood cells were removed by lysis followed by pelleting the harvested splenocytes.

Resuspended splenocytes were first incubated with FITC-anti-mFc and 5 nM biotinylated monomeric Erb3 protein (Erb3.mmh) for 1 hour. The stained cells were washed for 10 minutes with PBS, then stained with SA-PE for one hour. The stained cells were washed once with PBS and were analyzed by flow cytometry on a MoFlo (Cytomation).

Each IgG positive, antigen-positive B cell was sorted and plated into a separate well on a 384-well plate. RT-PCR of antibody genes from these B cells was performed according to a method described by Wang and Stollar (Journal of Immunological Methods 2000; 244: 217-225). Briefly, cDNAs for each single B cell were synthesized via reverse transcriptase (RT) reaction (Superscript™ III, Invitrogen). Each resulting RT product was then split and transferred into two corresponding wells on two 96-well plates. One set of the resulting RT products was first amplified by FOR using a 5' degenerate primer specific for human IgG heavy chain variable region leader sequence and a 3' primer specific for mouse heavy chain constant region, to form an amplicon. The amplicon was then amplified again by FOR using a 5' degenerate primer set specific for framework 1 of human IgG heavy chain variable region sequence and a 3' degenerate primer set specific for framework 4 of human IgG heavy chain variable region sequence. The other set of the resulting RT products was first amplified by FOR using a 5' degenerate primer specific for human kappa light chain variable region leader sequence and a 3' primer specific for mouse kappa light chain constant region to form an amplicon. The amplicon was then amplified again by FOR using a 5' degenerate primer set specific for framework 1 of human kappa light chain variable region sequence and a 3' degenerate primer set specific for framework 4 of human kappa light chain variable region sequence. The heavy chain and light chain PCR products were cloned into antibody vectors containing human IgG1 heavy chain constant region and kappa light chain constant region, respectively. The light chain expression plasmid has a loxP site and lox2272 site flanking the light chain expression cassette, and the heavy chain expression plasmid has a lox2272 site and a lox511 site flanking the heavy chain expression cassettes. Plasmids having either human heavy chain variable region sequence or human light chain variable region sequence were isolated from transformed E. coli cultures. Purified plasmids having a human heavy chain variable region sequence and plasmids having a human light chain variable region sequence from the same B cell were then combined and transfected into a modified EESYR® CHO host cell. Since the host CHO cell has, from 5' to 3', a loxP site, an eCFP, a lox2272 site, DsRed, and a lox511 site at the EESYR® locus, the host CHO cell can be isolated by flow cytometry as a blue-positive, red-positive, and green-negative cell. In addition, plasmids transiently expressing Cre were also transfected into the modified EESYR® CHO host cell. The transfected EESYR® CHO cells were sorted by flow cytometry. Proper recombinants that show blue-negative, red-negative, and green-positive cells were isolated and stable recombinant antibody expressing CHO cell lines were established from the isolated proper recombinants.

Example 5. Binding Affinity of Erb3 Antibodies to Erb3 Monomeric Protein

Binding affinities and kinetic constants of all 148 human monoclonal anti-Erb3 antibodies derived from B cells selected with 5 nM biotin-Erb3.mmh protein were determined by surface plasmon resonance at 25° C. Measurements were conducted on a Biacore 2000 instrument. Antibodies, expressed by transient transfection of CHO K1 cells as human IgG1, were captured on an anti-human Fc sensor surface, and soluble monomeric Erb3.mmh protein was injected over the surface. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) were calculated from the kinetic rate constants as: $K_D(M)=k_a/k_d$.

Figure 4:
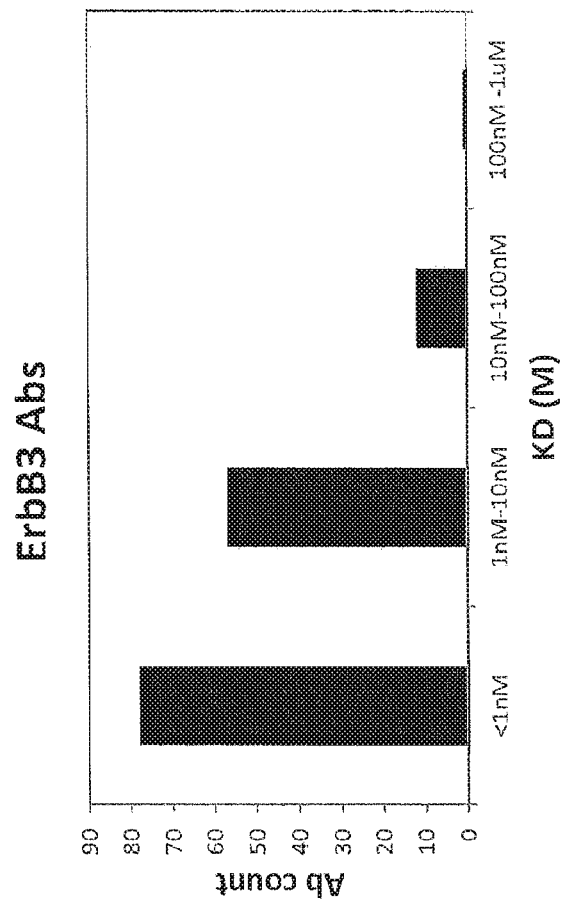
FIG. 4 illustrates the number of proportion of high-affinity antibodies (Abs) among the 148 anti-Erb3 antibodies isolated by selecting B cells with 5 nM biotin-Erb3.mmh protein by grouping the isolated Abs by their respective $K_D$ values, as follows: $K_D$s of less than 1 nM (78 Abs), $K_D$s between 1 nM to 10 nM (57 Abs), $K_D$s between 10 nM to 100 nM (12 Abs), and $K_D$s between 100 nM to 1 µM (1 Ab). Anti-Erb3 antibodies with less than 10 nM $K_D$ (135/148; over 91% of the isolated antibodies) significantly out-numbered antibodies with greater than 10 nM $K_D$.

FIG. 4 shows that among the 148 anti-Erb3 antibodies isolated by selecting B cells with 5 nM biotin-Erb3.mmh protein, 78 Abs bound Erb3.mmh with $K_D$s of less than 1 nM, 57 Abs bound Erb3.mmh with $K_D$s between 1 nM to 10 nM, 12 Abs bound Erb3.mmh with $K_D$s between 10 nM to 100 nM, and 1 Ab bound Erb3.mmh with $K_D$ between 100 nM to 1 μM. Anti-Erb3 antibodies with less than 10 nM $K_D$ significantly out-numbered antibodies with greater than 10 nM $K_D$, demonstrating that selecting and isolating B cells that bound 5 nM biotin-Erb3.mmh enriched for antibodies with high affinity (less than 10 nM $K_D$).

Nineteen (19) anti-Erb3 antibodies with the best affinity against Erb3.mmh were produced from stable EESYR® CHO cells and purified by protein A affinity chromatography.

Table 1 shows the affinities ($k_a$, $k_d$, $K_D$) and dissociation $t_{1/2}$ of the 19 purified Erb3 antibodies against Erb3.mmh or Erb3.mFc protein as determined by Biacore. Binding dissociation equilibrium constants ($K_D$) and dissociative half-lives ($t_{1/2}$) were calculated from the kinetic rate constants as: $K_D(M)=K_a/k_d$; and $t_{1/2}$ (min)=(ln 2/(60*$k_d$)).

TABLE 1

| Antibody Name | Analyte | $k_a$ | $k_d$ | $K_D$ | $t_{1/2}$ (min) |
|---|---|---|---|---|---|
| Erb-mAb1 | Erb3.mmh | 2.49E+06 | 5.96E−05 | 2.39E−11 | 179 |
|  | Erb3.mFc | 3.83E+06 | 3.95E−06 | 1.03E−12 | 2695 |
| Erb-mAb2 | Erb3.mmh | 3.72E+06 | 1.03E−04 | 2.78E−11 | 103 |
|  | Erb3.mFc | 5.16E+06 | 7.46E−06 | 1.45E−12 | 1429 |
| Erb-mAb3 | Erb3.mmh | 1.89E+06 | 1.37E−05 | 7.22E−12 | 780 |
|  | Erb3.mFc | 3.03E+06 | 1.37E−06 | 4.52E−13 | 7779 |
| Erb-mAb4 | Erb3.mmh | 1.14E+06 | 7.89E−05 | 6.90E−11 | 135 |
|  | Erb3.mFc | 2.21E+06 | 8 97E−06 | 4.06E−12 | 1188 |
| Erb-mAb5 | Erb3.mmh | 8.86E+05 | 4.88E−05 | 5.51E−11 | 218 |
|  | Erb3.mFc | 1.58E+06 | 2.26E−06 | 1.43E−12 | 4721 |
| Erb-mAb6 | Erb3.mmh | 1.95E+06 | 8.13E−05 | 4.18E−11 | 131 |
|  | Erb3.mFc | 2.96E+06 | 4.33E−06 | 1.46E−12 | 2458 |
| Erb-mAb7 | Erb3.mmh | 2.21E+06 | 1.18E−04 | 5.31E−11 | 91 |
|  | Erb3.mFc | 3.50E+06 | 8.69E−06 | 2.49E−12 | 1225 |
| Erb-mAb8 | Erb3.mmh | 9.29E+05 | 9.88E−05 | 1.06E−10 | 108 |
|  | Erb3.mFc | 1.48E+06 | 7.98E−06 | 5.41E−12 | 1335 |
| Erb-mAb9 | Erb3.mmh | 2.16E+06 | 3.81E−05 | 1.77E−11 | 279 |
|  | Erb3.mFc | 3.49E+06 | 3.35E−06 | 9.58E−13 | 3183 |
| Erb-mAb10 | Erb3.mmh | 2.39E+06 | 5.01E−05 | 2.09E−11 | 213 |
|  | Erb3.mFc | 3.71E+06 | 5.46E−06 | 1.47E−12 | 1952 |
| Erb-mAb11 | Erb3.mmh | 1.66E+06 | 3.27E−05 | 1.98E−11 | 326 |
|  | Erb3.mFc | 2.51E+06 | 9.86E−07 | 3.93E−13 | 10797 |
| Erb-mAb12 | Erb3.mmh | 1.83E+06 | 9.73E−05 | 5.31E−11 | 109 |
|  | Erb3.mFc | 2.86E+06 | 4.63E−06 | 1.75E−12 | 2302 |
| Erb-mAb13 | Erb3.mmh | 2.79E+06 | 3.46E−05 | 1.24E−11 | 308 |
|  | Erb3.mFc | 4.54E+06 | 1.98E−06 | 4.35E−13 | 5392 |
| Erb-mAb14 | Erb3.mmh | 2.47E+06 | 1.08E−04 | 4.38E−11 | 98 |
|  | Erb3.mFc | 3.33E+06 | 4.58E−06 | 1.50E−12 | 2325 |
| Erb-mAb15 | Erb3.mmh | 3.98E+06 | 3.47E−05 | 8.71E−12 | 307 |
|  | Erb3.mFc | 5.91E+06 | 1.74E−06 | 2.95E−13 | 6110 |
| Erb-mAb16 | Erb3.mmh | 3.04E+06 | 2.86E−05 | 9.42E−12 | 372 |
|  | Erb3.mFc | 4.48E+06 | 9.52E−07 | 2.13E−13 | 11186 |
| Erb-mAb17 | Erb3.mmh | 2.94E+06 | 3.43E−05 | 1.17E−11 | 311 |
|  | Erb3.mFc | 3.67E+06 | 1.24E−06 | 3.37E−13 | 8603 |
| Erb-mAb18 | Erb3.mmh | 2.13E+06 | 3.73E−05 | 1.76E−11 | 285 |
|  | Erb3.mFc | 3.25E+06 | 9.77E−07 | 3.00E−13 | 10901 |
| Erb-mAb19 | Erb3.mmh | 5.82E+05 | 6.72E−05 | 1.15E−10 | 159 |
|  | Erb3.mFc | 8.00E+05 | 1.13E−05 | 1.40E−11 | 945 |

Example 6. Isolation and Production of High Affinity Nerve Growth Factor (NGF) Antibodies Methods and procedures for isolation and production of high affinity anti-NGF antibodies were the same as those described in the Erb3 example (Example 4), except that human NGF protein was used as the immunogen and 5 nM of biotinylated NGF was used for selecting B cells.

Example 7. Binding Affinity of NGF Antibodies to NGF Protein

Binding affinities and kinetic constants of all 63 human monoclonal anti-NGF antibodies derived from B cells selected with 5 nM biotin-NGF protein were determined by surface plasmon resonance at 25° C. Measurements were conducted on a Biacore 2000 instrument. Antibodies, expressed by transient transfection of CHO K1 cells as human IgG1, were captured on an anti-human Fc sensor surface, and human NGF protein was injected over the surface. Kinetic association ($K_a$) and dissociation ($k_d$) were determined by processing and fitting the data to a 1:1 binding model using Scrubber 2.0 curve fitting software. Binding dissociation equilibrium constants ($K_D$) were calculated from the kinetic rate constants as: $K_D(M)=k_d/k_a$.

Figure 5:
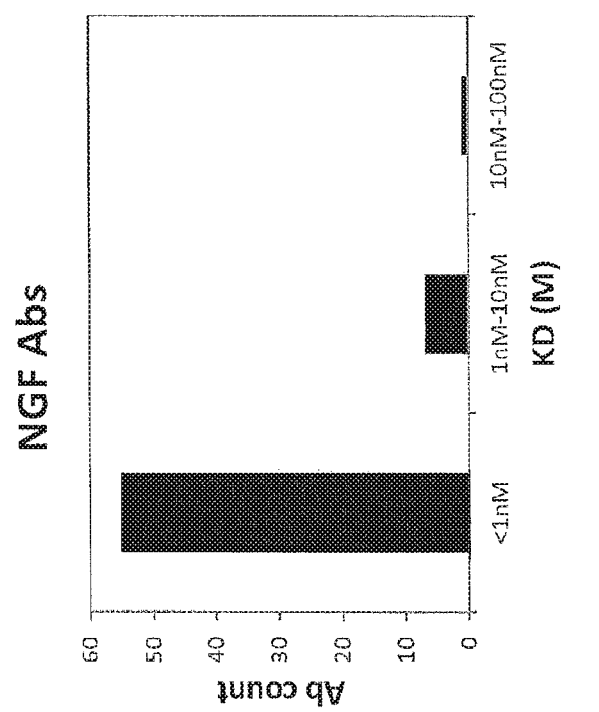
FIG. 5 illustrates the proportion of high-affinity antibodies (Abs) among the 63 anti-NGF antibodies isolated by selecting B cells with 5 nM biotin-NGF protein by grouping the isolated Abs by their respective $K_D$ values, as follows: $K_D$s of less than 1 nM (55 Abs), $K_D$s between 1 nM to 10 nM (7 Abs), and $K_D$s between 10 nM to 100 nM (1 Ab). Anti-NGF antibodies with less than 10 nM $K_D$ (62/63; over 98% of the isolated antibodies) significantly out-numbered antibodies with greater than 10 nM $K_D$.

FIG. 5 shows that among the 63 anti-NGF antibodies isolated by selecting B cells with 5 nM biotin-NGF, 55 Abs bound NGF with KDs of less than 1 nM, 7 Abs bound NGF with KDs between 1 nM to 10 nM, and 1 Ab bound NGF with KDs between 10 nM to 100 nM. Anti-NGF antibodies with less than 10 nM KD significantly out-numbered antibodies with greater than 10 nM KD, demonstrating that selecting and isolating B cells that bound 5 nM biotin-NGF enriched for antibodies with high affinity (less than 10 nM KD).

Twenty-one (21) anti-NGF antibodies with the highest affinity against NGF were produced from stable EESYR® CHO cells and purified by protein A affinity chromatography.

Table 2 shows the affinities ($k_a$, $k_d$, $K_D$) and dissociation $t_{1/2}$ of the 21 purified NGF antibodies against NGF protein as determined by Biacore. Binding dissociation equilibrium constants ($K_D$) and dissociative half-lives ($t_{1/2}$) were calculated from the kinetic rate constants as: $K_D(M)=k_d/k_a$; and $t_{1/2}$ (min)=(ln 2/(60*$k_d$).

TABLE 2

| Antibody ID | $k_a$ (1/Ms) | $k_d$ (1/s)* | $K_D$ (M) | $t_{1/2}$ (hrs) |
|---|---|---|---|---|
| NGF-mAb1 | 2.30E+07 | 2.63E−06 | 1.1E−13 | 73.2 |
| NGF-mAb2 | 1.65E+07 | 3.46E−06 | 2.1E−13 | 55.6 |
| NGF-mAb3 | 2.59E+07 | 1.09E−05 | 4.2E−13 | 17.7 |
| NGF-mAb4 | 3.57E+07 | 2.77E−05 | 7.1E−13 | 6.9 |
| NGF-mAb5 | 1.04E+07 | 5.56E−06 | 5.3E−13 | 34.6 |
| NGF-mAb6 | 5.81E+07 | 7.64E−06 | 1.3E−13 | 25.2 |
| NGF-mAb7 | 1.25E+07 | 1.32E−05 | 1.05E−12 | 14.6 |
| NGF-mAb8 | 2.44E+06 | 1.89E−04 | 7.76E−11 | 1.0 |
| NGF-mAb9 | 1.35E+07 | 6.66E−05 | 4.93E−12 | 2.9 |
| NGF-mAb10 | 3.39E+07 | 2.61E−04 | 7.68E−12 | 0.7 |
| NGF-mAb11 | 9.22E+06 | 3.94E−05 | 4.27E−12 | 4.9 |
| NGF-mAb12 | 7.27E+06 | 4.02E−05 | 5.53E−12 | 4.8 |
| NGF-mAb13 | 6.46E+06 | 4.86E−05 | 7.52E−12 | 4.0 |
| NGF-mAb14 | 1.88E+06 | 4.47E−05 | 2.38E−11 | 4.3 |
| NGF-mAb15 | 3.28E+06 | 3.20E−05 | 9.77E−12 | 6.0 |
| NGF-mAb16 | 5.87E+06 | 3.52E−04 | 6.01E−11 | 0.5 |
| NGF-mAb17 | 1.34E+07 | 1.00E−03 | 7.50E−11 | 0.2 |
| NGF-mAb18 | 7.05E+06 | 1.14E−03 | 1.62E−10 | 0.2 |
| NGF-mAb19 | 4.60E+06 | 8.73E−04 | 1.90E−10 | 0.2 |
| NGF-mAb20 | 1.74E+07 | 3.74E−06 | 2.2E−13 | 51.5 |
| NGF-mAb21 | 3.90E+06 | 1.14E−03 | 2.92E−10 | 0.2 |

Example 8. Isolation and Production of High Affinity Activin a Antibodies

Methods and procedures were the same as those described in the Erb3 example (Example 4) above; except that human Activin A protein was used as the immunogen and 1 nM of biotinylated Activin A was used for selecting B cells.

Example 9. Binding Affinity of Activin a Antibodies to Activin a Protein

Binding affinities of all 648 human monoclonal anti-Activin A antibodies derived from B cells selected with 1 nM biotin-Activin A protein were determined on a Biacore instrument. Antibodies, expressed by transient transfection of CHO K1 cells as human IgG1, were captured on an anti-human Fc sensor surface, and human Activin A protein was injected over the. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) were calculated from the kinetic rate constants as: $K_D(M)=k_d/k_a$.

Figure 6:
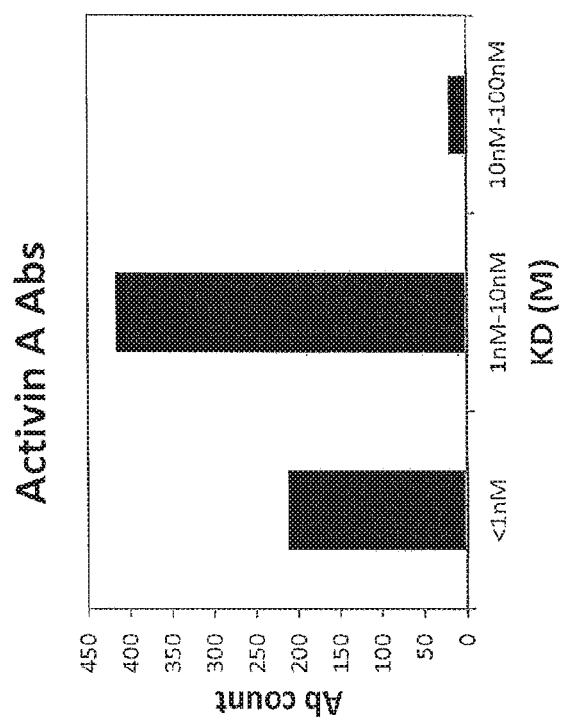
FIG. 6 illustrates the proportion of high-affinity antibodies (Abs) among the 648 anti-Activin A antibodies to Activin A protein isolated by selecting B cells with 1 nM biotin-Activin A protein by grouping the isolated Abs by their respective $K_D$ values, as follows: $K_D$s of less than 1 nM (212 Abs), $K_D$s between 1 nM to 10 nM (416 Abs), and $K_D$s between 10 nM to 100 nM (20 Abs). Anti-Activin A antibodies with less than 10 nM $K_D$ (628/648; over 96% of the isolated antibodies) significantly out-numbered antibodies with greater than 10 nM $K_D$.

FIG. 6 shows that among the 648 anti-Activin A antibodies isolated by selecting B cells with 1 nM biotin-Activin A, 212 Abs bound Activin A with KDs of less than 1 nM, 416 Abs bound Activin A with KDs between 1 nM to 10 nM, and 20 Abs bound Activin A with KDs between 10 nM to 100 nM. Anti-Activin A antibodies with less than 10 nM KD significantly out-numbered antibodies with greater than 10 nM KD, demonstrating that selecting and isolating B cells that bound 1 nM biotin-Activin A enriched for antibodies with high affinity (less than 10 nM KD).

Eighteen (18) anti-Activin A antibodies with the highest affinity against Activin A were produced from stable EESYR® CHO cells and purified by protein A affinity chromatography. Table 3 shows the affinities ($k_a$, $k_d$, $K_D$) and dissociation $t_{1/2}$ of the 18 purified antibodies against Activin A protein as determined by Biacore. Binding dissociation equilibrium constants (K©) and dissociative half-lives ($t_{1/2}$) were calculated from the kinetic rate constants as: $K_D(M)=k_d/k_a$; and $t_{1/2}$ (min)=(ln 2/(60*$k_d$).

TABLE 3

| Antibody | ka (Ms−1) | kd (s−1) | KD (Molar) | t½ (min) |
|---|---|---|---|---|
| Activin A-mAb1 | 3.33E+06 | 1.09E−04 | 3.26E−11 | 106.4 |
| Activin A-mAb2 | 3.14E+06 | 7.19E−04 | 2.29E−10 | 16 |
| Activin A-mAb3 | 1.18E+07 | 7.00E−04 | 5.95E−11 | 16 |
| Activin A-mAb4 | 7.82E+06 | 6.39E−05 | 8.17E−12 | 180.8 |
| Activin A-mAb5 | 4.75E+07 | 1.67E−04 | 3.52E−12 | 69 |
| Activin A-mAb6 | 1.57E+07 | 5.00E−05 | ≤3.18E−12 | ≥231 |
| Activin A-mAb7 | 1.42E+07 | 5.77E−04 | 4.06E−11 | 20 |
| Activin A-mAb8 | 8.85E+06 | 1.68E−04 | 1.90E−11 | 68.7 |
| Activin A-mAb9 | 1.58E+07 | 2.13E−03 | 1.34E−10 | 5 |
| Activin A-mAb10 | 1.20E+07 | 5.88E−04 | 4.92E−11 | 20 |
| Activin A-mAb11 | 3.76E+06 | 9.28E−05 | 2.47E−11 | 124.5 |
| Activin A-mAb12 | 1.10E+07 | 5.00E−05 | ≤4.55E−12 | ≥231 |
| Activin A-mAb13 | 2.40E+06 | 5.00E−05 | ≤2.08E−11 | ≥231 |
| Activin A-mAb14 | 1.29E+07 | 5.00E−05 | ≤3.88E−12 | ≥231 |
| Activin A-mAb15 | 2.36E+06 | 5.00E−05 | ≤2.12E−11 | ≥231 |
| Activin A-mAb16 | 4.76E+06 | 5.00E−05 | ≤1.05E−11 | ≥231 |
| Activin A-mAb17 | 4.69E+06 | 5.00E−05 | ≤1.07E−11 | ≥231 |
| Activin A-mAb18 | 7.86E+06 | 5.00E−05 | ≤6.36E−12 | ≥231 |

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

We claim:

1. A method for selecting primary antibody-producing cells that express antibodies exhibiting high affinity binding for an antigen of interest, the method comprising:
   (a) contacting a population of primary antibody-producing cells that express antibody to the antigen of interest with a monomeric form of the antigen of interest for a time sufficient for the antigen of interest to bind to antibody on the surface of the cells, wherein the concentration of the monomeric antigen of interest is between 0.1-2 nM or between 5-10 nM;
   (b) washing the cells for a period of time to remove unbound antigen;

(c) collecting cells bound to the antigen of interest; and
(d) sorting the cells collected in step (c) to obtain cells that express antibodies of high affinity, wherein the high affinity antibodies have a dissociation equilibrium constant (KD) of 0.1 pM to 25 nM.

2. The method of claim 1, wherein the primary antibody-producing cells express antibody that is membrane-bound antibody.

3. The method of claim 1, wherein the antigen comprises a detectable label.

4. The method of claim 3, wherein the detectable label is conjugated directly to the antigen.

5. The method of claim 4, wherein the detectable label is conjugated to antigen via a pair of binding partners.

6. The method of claim 5, wherein one binding partner of the pair of binding partners is labeled with a detectable label.

7. The method of claim 5, wherein the pair of binding partners is biotin/streptavidin.

8. The method of claim 3, wherein the antigen is biotinylated and the biotinylated antigen is contacted with streptavidin comprising the detectable label.

9. The method of claim 8, wherein cells that bind the biotinylated antigen are contacted with the streptavidin after step (b).

10. The method of claim 3, wherein the detectable label is a fluorescent label.

11. The method of claim 10, wherein step (c) comprises using fluorescence-activated cell sorting to collect the cells bound to the antigen of interest.

12. The method of claim 10, wherein step (d) comprises sorting the cells by flow cytometry.

13. The method of claim 12, wherein the cells are sorted into at least two populations of cells using fluorescence-activated cell sorting according to fluorescence intensity.

14. The method of claim 13, wherein antibody affinity is determined by surface plasmon resonance or solution-affinity enzyme-linked immunosorbent assay (ELISA).

15. The method of claim 1, wherein the cells sorted in step (d) are sorted as single cells.

16. The method of claim 1, further comprising step (e), which comprises:
(i) isolating an antibody-encoding nucleic acid from the cells that express antibodies of high affinity of step (d);
(ii) transfecting a host cell with a vector comprising the antibody-encoding nucleic acid; and
(iii) growing the transfected host cell under conditions to support expression of antibody by the host cell.

17. The method of claim 16, wherein the vector is an expression vector.

18. The method of claim 16, wherein the host cell is Chinese hamster ovary (CHO) cell.

19. The method of claim 16, wherein the antibody comprises a human heavy chain variable region and a human light chain variable region.

20. The method of claim 19, wherein the antibody further comprises a human heavy chain constant region and a human light chain constant region.

21. The method of claim 19, wherein the human heavy chain variable region is a human IgG heavy chain variable region.

22. The method of claim 19, wherein the human light chain variable region is a human kappa light chain variable region.

23. The method of claim 19, wherein the concentration of monomeric antigen is between 0.1 nM and 2.0 nM.

24. The method of claim 19, wherein the concentration of monomeric antigen is between 5 nM and 10 nM.

25. The method of claim 1, wherein the high-affinity antibodies comprise a human heavy chain variable region and human a light chain variable region.

26. The method of claim 25, wherein the human heavy chain variable region is a human IgG heavy chain variable region.

27. The method of claim 25, wherein the human light chain variable region is a human kappa light chain variable region.

28. The method of claim 25, wherein the wherein the concentration of monomeric antigen is between 0.1 nM and 2.0 nM.

29. The method of claim 28, wherein the concentration of monomeric antigen is 1 nM.

30. The method of claim 1, wherein the high affinity antibodies have a $K_D$ of from 0.1 pM to 10 nM.

31. The method of claim 30, wherein the high affinity antibodies have a $K_D$ of from 0.1 nM to 10 nM.

32. The method of claim 1, wherein the population of primary antibody-producing cells is derived from antibody-producing cells obtained from a human that has been exposed to the antigen of interest.

33. The method of claim 32, wherein the antibody-producing cells are obtained from peripheral blood of a human with humoral immunity to the antigen of interest.

34. The method of claim 33, wherein the antibody-producing cells are peripheral blood mononuclear cells (PBMCs).

35. The method of claim 32, wherein the population of human primary antibody-producing cells comprises lymphocytes selected from the group consisting of B-cells, memory B-cells and plasmablasts.

36. The method of claim 1, wherein the population of primary antibody-producing cells is derived from antibody-producing cells obtained from a non-human mammal.

37. The method of claim 36, wherein the antibody-producing cells are obtained from a non-human mammal with humoral immunity to the antigen of interest.

38. The method of claim 36, wherein the antibody-producing cells are obtained from spleen, lymph node, bone marrow or peripheral blood of the non-human mammal.

39. The method of claim 36, wherein the non-human mammal comprises a nucleic acid sequence encoding a human heavy chain variable region and a nucleic acid sequence encoding a human light chain variable region.

40. The method of claim 1, wherein the period of time for washing the cells is 60 minutes or less.

41. The method of claim 1, wherein the concentration of monomeric antigen is between 5 nM and 10 nM.

42. The method of claim 1, wherein the concentration of monomeric antigen is 5 nM.

43. The method of claim 1, wherein the concentration of monomeric antigen is between 0.1 and 2 nM.

44. The method of claim 43, wherein the concentration of monomeric antigen is 1 nM.

45. The method of claim 44, wherein the concentration of monomeric antigen is between 0.1 to 1 nM.

46. The method of claim 43, wherein the concentration of monomeric antigen is 2 nM.

47. The method of claim 1, wherein at least 90% of the cells sorted in step (d) express high-affinity antibodies.

* * * * *

UNITED STATES PATENT AND TRADEMARK OFFICE
CERTIFICATE OF CORRECTION

PATENT NO. : 11,808,766 B2
APPLICATION NO. : 16/987639
DATED : November 7, 2023
INVENTOR(S) : Gang Chen et al.

It is certified that error appears in the above-identified patent and that said Letters Patent is hereby corrected as shown below:

In the Claims

Column 20, Claim 44 should read:
45. The method of claim 44, wherein the concentration of monomeric antigen is 1 nM.

Column 20, Claim 45 should read:
44. The method of claim 43, wherein the concentration of monomeric antigen is between 0.1 to 1 nM.

Signed and Sealed this
Thirteenth Day of February, 2024

Katherine Kelly Vidal
*Director of the United States Patent and Trademark Office*